(12) United States Patent
Kato et al.

(10) Patent No.: US 6,315,888 B1
(45) Date of Patent: Nov. 13, 2001

(54) METHOD OF CONSTANT-CURRENT POLARIZATION VOLTAGE AND APPARATUS FOR KARL-FISCHER TECHNIQUE

(75) Inventors: Hiromasa Kato, Yokohama; Masafumi Nakatani, Chigasaki, both of (JP)

(73) Assignees: Mitsubishi Chemical Corporation, Tokyo; Dia Instruments Co., Ltd., Chigasaki, both of (JP)

( * ) Notice: Subject to any disclaimer, the term of this patent is extended or adjusted under 35 U.S.C. 154(b) by 0 days.

(21) Appl. No.: 09/509,818

(22) PCT Filed: Aug. 17, 1999

(86) PCT No.: PCT/JP99/04420

§ 371 Date: Apr. 18, 2000

§ 102(e) Date: Apr. 18, 2000

(87) PCT Pub. No.: WO00/11460

PCT Pub. Date: Mar. 2, 2000

(30) Foreign Application Priority Data

Aug. 18, 1998 (JP) ................................... 10-231331
Dec. 25, 1998 (JP) ................................... 10-369382

(51) Int. Cl.⁷ .................................................. G01N 27/44
(52) U.S. Cl. ....................... 205/788.5; 205/788; 204/405; 422/77; 436/42
(58) Field of Search ................................ 205/778.5, 788, 205/788.5; 204/405; 422/75, 76, 77, 82.08; 436/42

(56) References Cited

U.S. PATENT DOCUMENTS

| | | | |
|---|---|---|---|
| 4,582,572 | * | 4/1986 | Ishikawa ................................ 422/77 |
| 4,664,756 | | 5/1987 | Shimizu et al. . |
| 4,741,815 | * | 5/1988 | Bercik et al. ........................ 204/405 |

FOREIGN PATENT DOCUMENTS

| | | |
|---|---|---|
| 54-25895 | 2/1979 | (JP) . |
| 59-210355 | 11/1984 | (JP) . |
| 61-20853 | 1/1986 | (JP) . |
| 62-39749 | 2/1987 | (JP) . |
| 3-4160 | 1/1991 | (JP) . |
| 5-10923 | 1/1993 | (JP) . |

* cited by examiner

Primary Examiner—Robert J. Warden, Sr.
Assistant Examiner—Kaj K. Olsen
(74) Attorney, Agent, or Firm—Oblon, Spivak, McClelland, Maier & Neustadt, P.C.

(57) ABSTRACT

A constant-current polarization voltage detecting method includes step of feeding to a detecting electrode a predetermined minute current in a pulse form, and detecting sequentially a polarization voltage at each time of feeding the pulsating current, in an electrochemical analysis in solution. The polarization voltage is detected after a lapse of a predetermined time from the initiation of feeding the pulsating current at each time. A Karl Fischer's moisture content analyzing apparatus can utilize such a method.

14 Claims, 3 Drawing Sheets

METHOD OF CONSTANT-CURRENT POLARIZATION VOLTAGE AND APPARATUS FOR KARL-FISCHER TECHNIQUE

BACKGROUND OF THE INVENTION

1. Field of the Invention

The present invention relates to a constant-current polarization voltage detecting method used suitably in a Karl Fischer's moisture content measuring method and a Karl Fischer's moisture content measuring apparatus using such detecting method.

2. Discussion of the Background

For a detecting means to measure a moisture content for which a Karl Fischer's (hereinbelow, referred to as "KF") volumetric titration method of this kind is used, a so-called constant-current polarization voltage detecting method has often been employed in recent years. Namely, in the constant-current polarization voltage detecting method, a minute current is fed to dual platinum electrodes, as a detecting electrode, to measure a voltage across the dual platinum electrodes. In this case, although a minute current to be fed can either be a direct current or an alternating current, a pulse-like current has recently been used.

On the other hand, when a titration solvent composed mainly of chloroform as solvent was used for the constant-current polarization voltage detecting method, there was in fact difficulty in conducting the measurement of a large amount of sample in a moisture content measuring apparatus by a conventional technique. This was because the monitoring of a polarization voltage could not properly be effected since the liquid resistance of a chloroform solvent is high, and the liquid resistance is further increased by the incorporation of a large amount of sample having no-polarization properties in the titration solvent.

The moisture content measurement using the above-mentioned KF volumetric titration method is such one utilizing KF titration reactions as follows:

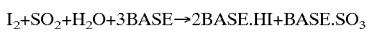

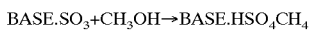

wherein BASE: an amine compound

Namely, in the titration reactions in the moisture content measurement by the KF volumetric titration method, since the reaction with water accelerates selectively, a wide application has conventionally been made for the measurement of moisture content. In this case, in a KF volumetric titration method, measurement is carried out by using an iodine-containing solution as titrant. In a coulometric titration method, iodine is generated by anode oxidation of iodide ions. Thus, the above-mentioned reactions are effected. In either method of detection, the end point of titration is recognized when an excessive amount of iodine is detected on the detecting electrode.

In such detecting method for detecting an excessive iodine, the above-mentioned constant-current polarization voltage detecting method is generally used, wherein according to the volumetric titration method, the titration is finished at the time when a state that an amount of iodine is excessive (a state a potential which is lower than that at the end point) continues 30 seconds, and according to the coulometric titration method, the titration is finished at the time when a potential is beyond the potential at the end point at which a state of a slight iodine being excessive can be detected.

Generally, there is no problem in a conventional titration method even when solvent containing much methanol is used as a titration solvent, and the titration is conducted by using a KF reagent. Even though any sample is incorporated, it is possible to reach the end point if the KF reagent is dropped excessively, and the moisture content measurement can be conducted regularly.

However, in a case of measuring oils, the titration is usually conducted in a titration solvent containing chloroform as a main solvent because the oils do not dissolve in methanol. However, since oils generally have a small moisture content, a large amount of sample is to be poured into the titration solvent. In this case, the presence of a much amount of chloroform increases the liquid resistance of the titration solvent. The incorporation of a much amount of sample further increases the liquid resistance. Under such condition, when a predetermined minute current of pulse form is applied, an apparent polarization voltage is assumed to be the sum of the true polarization voltage and a polarization voltage resulted from the liquid resistance. Accordingly, even though the titration in fact reaches the end point of titration, there is found a phenomenon as if it does not reach the end point of titration.

SUMMARY OF THE INVENTION

The present invention is to solve the problems in the conventional technique, and aims at providing a constant-current polarization voltage detecting method for measuring a moisture content by a KF titration reaction wherein the detection or the monitoring of a polarization voltage under a regular condition can be conducted, and a Karl Fischer's moisture content measuring apparatus using such method.

In order to achieve the above-mentioned object, the inventors of this application have made various studies, to improve the above-mentioned problems, on the constant-current polarization voltage detecting method for measuring a moisture content in the KF titration reaction, as the result of which they have found an important fact. Namely, influence to a polarization voltage due to solvent, when a current is applied in a pulse form, is usually large immediately after the application.

Description will be made in the following as to the result of the studies. FIG. 1 is a diagram showing a relation of time to polarization voltage in Karl Fischer's moisture content measurement using the constant-current polarization voltage detecting method. In this case, determination is made so that a cycle of the application of a pulsating minute current is 500 ms and the pulse width of the current actually applied is 50 ms.

As shown in FIG. 1, when an ordinarily used sample is measured with a methanol type solvent, a polarization voltage measured on a detecting electrode increases gradually under the condition of the moisture content being excessive, and it decreases when the applied current is stopped.

When a KF reagent containing iodine is dropped to titrate a moisture content, an increase of polarization voltage tends to gradually decrease to thereby cause the KF reagent becoming excessive, with the result that the polarization voltage becomes very low. In this case, in a commercially available moisture content measuring apparatus using a volumetric method, an end point of analysis is determined when a polarization voltage, which has been detected as it is, takes a predetermined value (i.e., a value at the time when the KF reagent becomes excessive. This expression is applicable hereinbelow). Or, the end point is so determined that a waveform of a polarization voltage in a time is detected; an integration value of the polarization voltage in a one cycle (the surface area of a hatched portion in FIG. 1) is detected, and the integration value reaches a predetermined value at which the end point is determined.

On the other hand, in the measurement of a moisture content in oils, since oils are insoluble to methanol, solvent containing chloroform as the main solvent is used. As described above, however, since the solvent containing chloroform as the main solvent has a high liquid resistance, a detected voltage is the sum of a voltage due to the liquid resistance and a true polarization voltage. Further, when a sample is added to the solvent, the influence of the liquid resistance becomes remarkable. As clear from FIG. 1, it is understood that the polarization voltage shows an abnormal pattern just after the application of a pulsating current. Although the dropping of the KF reagent to titrate a moisture content reduces somewhat the polarization voltage, a value lower than a certain value can not be expected. As a result, although the moisture content in the sample has been able to be titrated by the KF reagent, the dropping of the KF reagent is continued because a polarization voltage does not decrease to a voltage at the end point (or an integration value of polarization voltage).

In consideration of these circumstances of the measurement of moisture content by the KF titration reaction using the above-mentioned constant-current polarization voltage detecting method, the inventors have made effort to eliminate an adverse effect to a polarization voltage due to the solvent, and have completed the present invention by removing a polarization voltage produced just after the application of a pulsating minute current whereby a polarization voltage close to the true value can be detected.

Namely, in accordance with a first aspect of the present invention, there is provided a constant-current polarization voltage detecting method comprising feeding to a detecting electrode a predetermined minute current in a pulse form, and detecting sequentially a polarization voltage at each time of feeding the pulsating current, in an electrochemical analysis in solution, the constant-current polarization voltage detecting method being characterized in that the polarization voltage is detected after a lapse of a predetermined time (to) from the initiation of feeding the pulsating current at each time.

According to a second aspect, there is provided a constant-current polarization voltage detecting method comprising feeding to a detecting electrode a predetermined minute current in a pulse form, and detecting sequentially a polarization voltage at each time of feeding the pulsating current, in a Karl Fischer's moisture content analysis, the constant-current polarization voltage detecting method being characterized in that a polarization voltage difference (X–Xo) obtained by subtracting a polarization voltage (Xo) after a lapse of a predetermined time (to) from the initiation of feeding the pulsating current at each time, from a polarization voltage (X) at each time of feeding the pulsating current, is detected.

According a third aspect, there is provided a Karl Fischer's moisture content measuring apparatus using a constant-current polarization voltage detecting method, the Karl Fischer's moisture content measuring apparatus being characterized by comprising means for feeding a constant current in a pulse form to a detecting electrode immersed in a reaction liquid, means for detecting sequentially a polarization voltage (X) during the feeding of the current, means for calculating a value (X–Xo) obtained by subtracting a polarization voltage (Xo) after a lapse of time (to) from the initiation of feeding the pulsating current at each time, from a polarization voltage (X) at each time of feeding the pulsating current detected sequentially, means for determining the end point of measurement of moisture content by using the polarization voltage difference (X–Xo), and means for calculating a moisture content concentration from a result of calculation.

Hereinbelow, description will be made in detail as to the constant-current polarization voltage detecting method and the Karl Fischer's moisture content measuring apparatus according to the present invention.

The Karl Fischer's (hereinbelow, referred to as "KF") moisture content measuring apparatus used in the present invention is shown in, for example, FIG. 3.

The apparatus comprises a titration section and a measuring/displaying section wherein the titration section comprises a titration flask and a KF reagent titration device, and the measuring/displaying section comprises a detecting section, a data processing section and a control section.

A KF reactive solvent is received in the titration flask. The KF reactive solvent can be used without particular limitation as far as it can be used for an ordinary KF moisture content measurement. However, when a reactive solvent having a high liquid resistance such as a chloroform series solvent or the like is used, the effect of the present invention is in particular remarkable. For example, the present invention provides an excellent effect in a case that a KF reactive solvent containing chloroform of more than 30% is used. A detecting electrode is immersed in the reactive solvent. A minute current of pulse-like form is applied to the detecting electrode. The application of the pulsating current means that, as shown in FIG. 2, an applicable cycle is formed of a predetermined time of current feeding and a predetermined time of current stopping, and the cycle is repeated. The applicable cycle is preferably 100–3,000 ms, more preferably, 300–700 ms. The pulse width of the current fed to the defecting electrode is preferably 10–1,000 ms, more preferably 10–100 ms. An applicable current is preferably 3–100 $\mu$A, more preferably, 3–30 $\mu$A. A sample to be measured is poured through the sample introducing port of the titration flask when the moisture content is to be measured.

After the introduction of the sample to be measured into the titration flask, a KF titration reagent including iodine is added with constant intervals from the KF reagent titration device into the titration flask. An amount of the titration reagent to be added in a time is controlled by the control section from which a signal is transmitted so that a pulse motor drives a piston buret, whereby the KF titration reagent is forced from the KF reagent titration device and is dropped through the titration nozzle. As a moisture content in the titration flask is larger, a much amount of the titration reagent is added. The addition of the titration reagent is conducted when the current is not applied to the detecting electrode.

FIG. 2 is a diagram showing a relation of time to polarization voltage in order to explain the detecting method of the present invention.

The detecting section has a mechanism for applying a minute current to the detecting electrode immersed in the KF reactive solvent so that a polarization voltage (X) across electrodes in the detecting electrode is detected.

The data processing section calculates a value (X–Xo) which is obtained by subtracting a polarization voltage (Xo) after a lapse of a predetermined time (to) from the initiation of feeding the pulsating current at each time, from a value of polarization voltage (X) at each time of feeding the pulsating current detected sequentially. After a lapse of a predetermined time (to) from the initiation of feeding the current indicates the time at which an abnormal disturbance in the polarization voltage produced just after the application of a pulsating current to the detecting electrode has disappeared. For example, in view of a polarization voltage curve obtained by measuring a moisture content in an electrical insulation oil by using a highly chloroform-containing solvent in FIG. 2, the polarization voltage once drops just after the application of the current and then, increases. A predetermined time (to) indicates the time at which the polarization voltage begins rising to depict a smooth polarization voltage curve. Specifically, the predetermined time (to) from the initiation of feeding the current, which varies depending on conditions of measurement, is generally 0.1–200 ms, preferably, 0.1–50 ms, more preferably, 0.1–5 ms. For example, a polarization voltage is previously measured before the initiation of titration; the time at which a smooth polarization voltage curve is to be depicted is determined as "to", and the value of "to" is previously stored in a KF analyzing device. When a methanol series solvent is used, the value of "to" is optional. However, when a value of "to" is large, a value of polarization voltage difference (X–Xo) detected becomes small. Accordingly, it is preferable that the value of "to" is small from the viewpoint of accuracy. When a value of "to" suitable for using a highly chloroform-containing solvent is previously memorized in the analyzing device, the measurement of a moisture content can accurately be conducted with the same device even in a case of using the highly chloroform-containing solvent or a case of using a methanol series solvent.

Then, an integration value of polarization voltage difference (X–Xo) is calculated for every one cycle of feeding after a lapse of a predetermined time (to) from the initiation of feeding the current. The integration value is expressed by a hatched portion in the waveform of a polarization voltage in FIG. 2. Depending on the magnitude of the integration value in one cycle, an amount of the reagent for titration from the KF reagent titration device is controlled by the control section. When the integration value reaches a previously determined value (a value in a state that the KF titration reagent becomes excessive), the end point of analysis is determined, and the dropping of the reagent is stopped. The predetermined value is previously inputted into the measuring device by measuring separately a value in a state that the KF is excessive. As to the way of determining the predetermined value, for example, a methanol series solvent having a low liquid resistance is used as the KF reactive solvent, and an integration value in a state that the KF titration reagent is excessive is measured.

After the completion of the titration, a moisture content in a sample to be measured is calculated in the data processing section based on an amount of the KF titration reagent used, and a calculated value is outputted.

The above-mentioned end point determining method is a method to determine the end point with use of an integration value of polarization voltage difference. However, the end point may be determined when the polarization voltage difference (X–Xo) reaches a predetermined value. However, the way of determination with an integration value is preferred because of improving accuracy in analysis.

Further, description has been made exemplifying the volumetric titration method. However, the present invention is usable for a coulometric titration method, and an analyzing method using the coulometric titration method and an apparatus using the same are included in the scope of the present invention as far as they are not beyond the description.

DESCRIPTION OF THE PREFERRED EMBODIMENTS

EXPERIMENTAL EXAMPLE 1

Figure 1A:
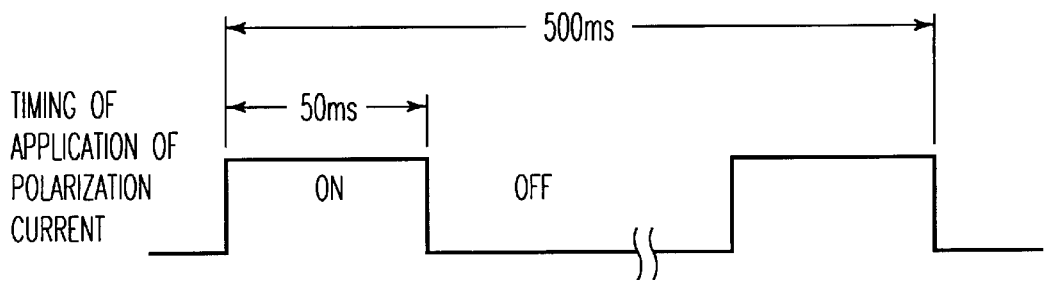
FIG. 1 is a diagram showing an example of a polarization voltage curve in a case that a current is fed in a pulse form to a detecting electrode in a constant-current polarization voltage detecting method wherein integrated portions monitored by a conventional moisture content end point detecting method are shown.
Figure 1B:
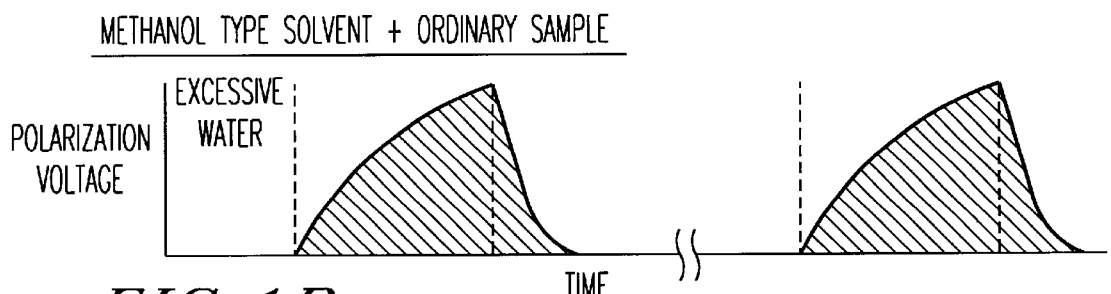
Figure 1C:
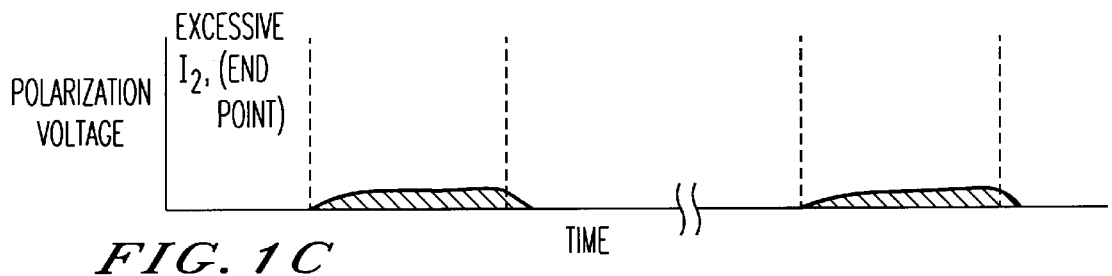
Figure 1D:
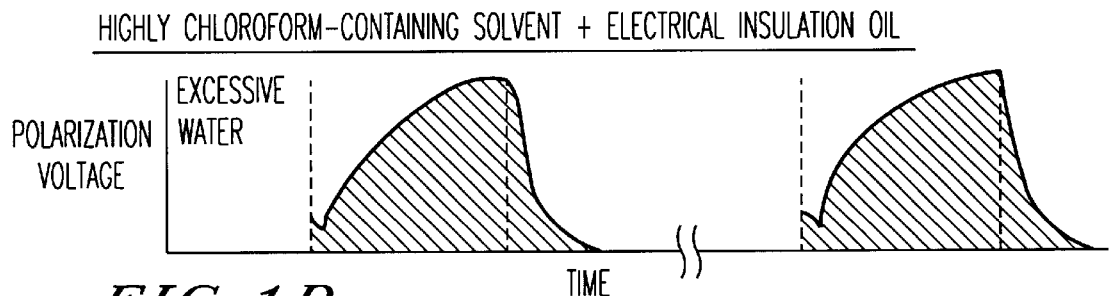
Figure 1E:
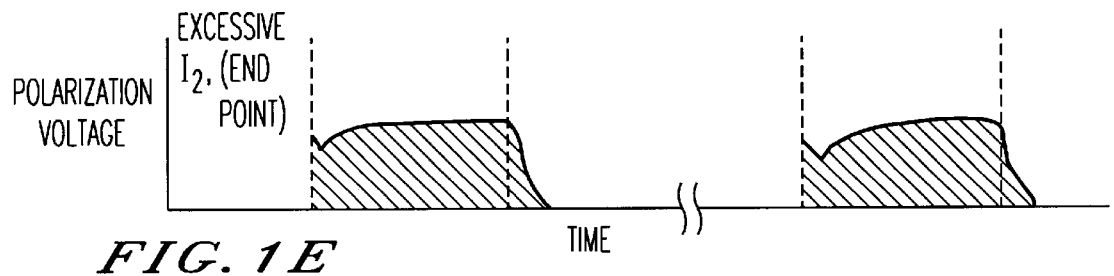
Figure 2A:
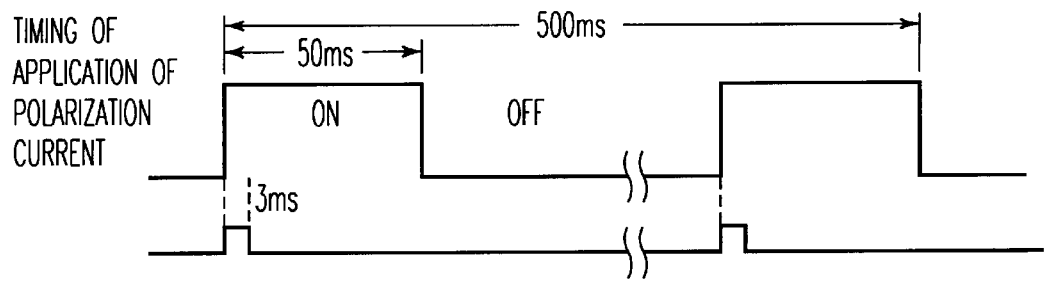
FIG. 2 is a diagram showing an example of a polarization voltage curve in a case that a current is fed in a pulse form to the detecting electrode in the constant-current polarization voltage detecting method wherein integrated portions monitored according to the present invention are shown.
Figure 2B:
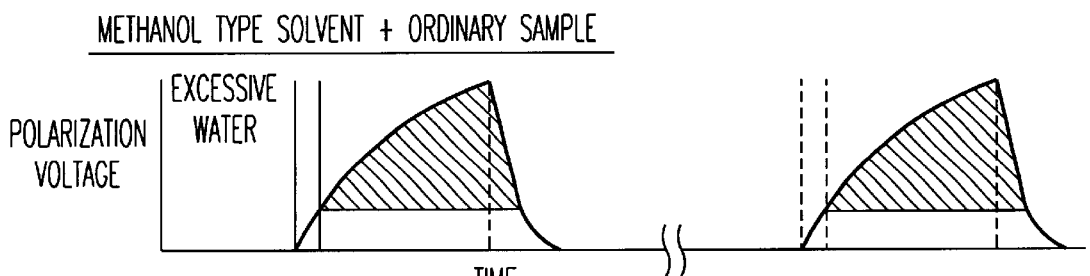
Figure 2C:
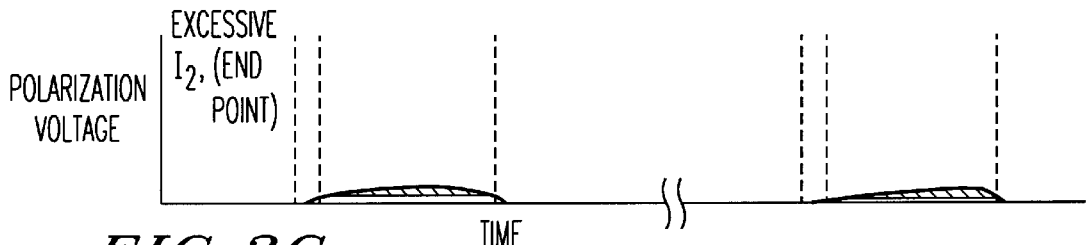
Figure 2D:
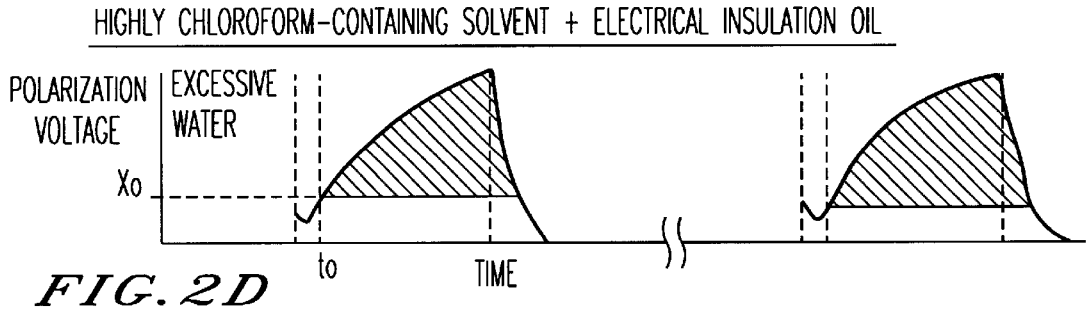
Figure 2E:
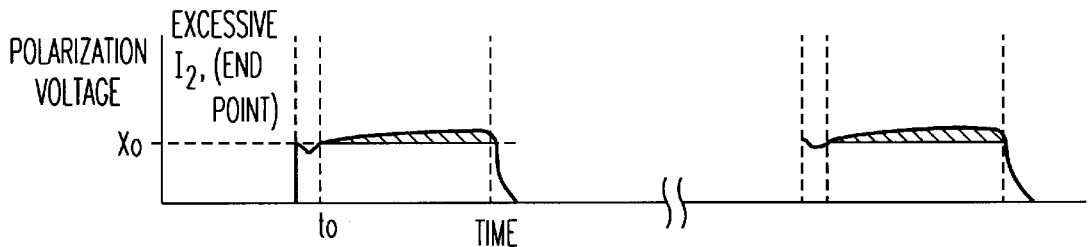
Figure 3:
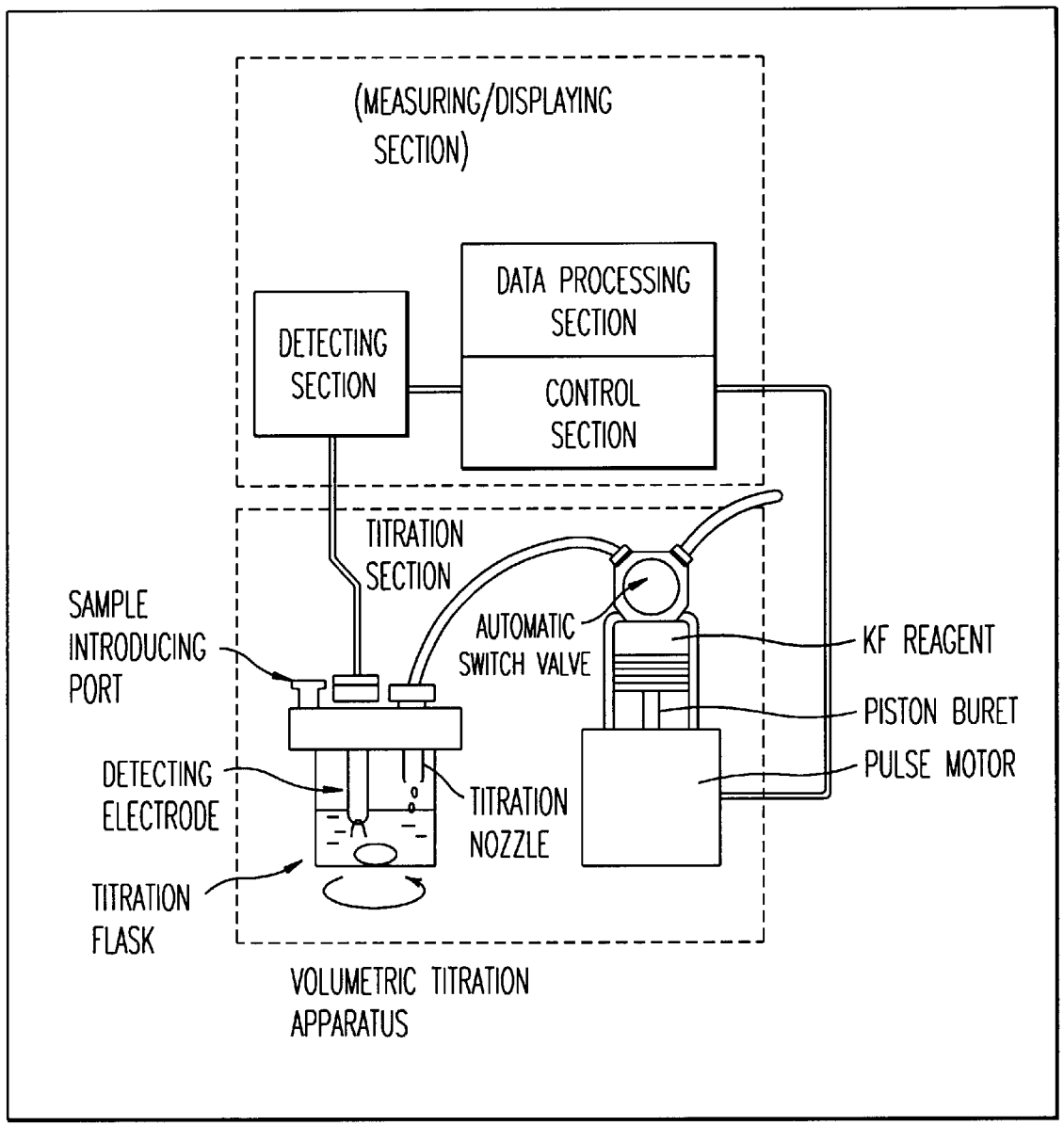
FIG. 3 is a diagram showing an example of a KF analyzing device used in the present invention.

A moisture content in an electrical insulation oil was measured with use of the KF moisture content measuring device shown in FIG. 3. First, 50 ml of a dehydrated solvent CM (manufactured by Mitsubishi Chemical Corporation, the content of chloroform: 87%) was charged into a titration flask, and a previous titration was conducted with KF reagent SS 3 mg (manufactured by Mitsubishi Chemical Corporation) to remove water in the titration flask. Then, each amount of 20 ml of the electrical insulation oil was measured. A current of 25 $\mu$A was applied to the detecting electrode wherein a cycle of the application of the current was 500 ms and a pulse width of the applied current was 25 ms. A polarization voltage (X) during the feeding of the current was sequentially detected, and a value (X–Xo) obtained by subtracting a polarization voltage (Xo) after a lapse of 1 ms from the initiation of feeding the pulsating current at each time, from the polarization voltage (X) during the feeding of the current detected sequentially, was calculated. The end point of analysis was determined at the time when an integration value (the surface area of a hatched portion in FIG. 2) of the polarization voltage difference (X–Xo), in one cycle of current feeding, after a lapse of 1 ms from the initiation of feeding the current reached a predetermined value (a value in a state that the KF reagent became excessive), and then, a moisture content in the electrical insulation oil was calculated.

COMPARATIVE EXAMPLE 1

The measurement was conducted in the same manner as Example 1 except that the end point of analysis was determined at the time when an integration value (the surface area of a hatched portion in FIG. 1), in a one time of current feeding, of the polarization voltage (X) from the initiation of feeding the current reached a predetermined value (a value in a state that the KF reagent became excessive).

Results of Example 1 and Comparative Example 1 are shown in Table 1.

TABLE 1

| | Result of measurement | | | |
|---|---|---|---|---|
| | Quantity of sample | Moisture content | Time | Analyzed value |
| Moisture content measuring apparatus of the present invention | 17.3145 g | 0.604 mg | 1'54" | 35 ppm |
| | 17.1783 g | 0.572 mg | 1'18" | 33 ppm |
| | 17.2235 g | 0.527 mg | 1'40" | 31 ppm |
| | Av: 33 ppm | | RSD: 6.6% | |
| Moisture content measuring apparatus of a conventional example | 17.0075g | It does not reach the end point | | |

EXPERIMENTAL EXAMPLE 2

50 ml of dehydrated solvent OLII (manufactured by Mitsubishi Chemical Corporation, the content of chloroform: 82%) was charged into a titration flask, and a previous titration was conducted with KF reagent SS-X 3 mg (manufactured by Mitsubishi Chemical Corporation) to remove water in the titration flask. Then, each amount of 10 ml of Kerosene was measured. The other conditions for measurement were the same as those in Example 1.

COMPARATIVE EXAMPLE 2

The measurement was conducted in the same manner as Example 2 except that the conventional end point determining method described in Comparative Example 1 was used. Results of Example 2 and Comparative Example 2 are shown in Table 2.

TABLE 2

|  | Result of measurement | | | |
| --- | --- | --- | --- | --- |
|  | Quantity of sample | Moisture content | Time | Analyzed value |
| Moisture content measuring apparatus of the present invention | 7.7091 g | 0.348 mg | 0'56" | 45 ppm |
|  | 7.9134 g | 0.388 mg | 1'04" | 49 ppm |
|  | 7.3733 g | 0.403 mg | 1'37" | 55 ppm |
|  | 7.6924 g | 0.336 mg | 1'05" | 44 ppm |
|  | 7.6784 g | 0.307 mg | 1'34" | 40 ppm |
|  | Av: 47 ppm | | | RSD: 12% |
| Moisture content measuring apparatus of a conventional example | 7.8415 g | 0.336 mg | 0'37" | 43 ppm |
|  | 7.6985 g | 0.552 mg | 0'41" | 72 ppm |
|  | 7.7132 g | It does not reach the end point | | |

As is clear from the above experimental Examples 1 and 2, the KF titration was normally progressed even by using the solvent containing chloroform as the major solvent, and a correct moisture content measurement of a sample containing a much amount of oil, for which the measurement was impossible, became possible.

As described in detail, according to the constant-current polarization voltage detecting method and the apparatus using the method in the present invention, the monitoring of a polarization voltage can be conducted wherein influence to the polarization voltage due to solvent can effectively and sufficiently be eliminated, whereby the measurement of moisture content can effectively and correctly be conducted. Further, there is an excellent feature that the method can easily be conducted since the above-mentioned method itself is very simple.

What is claimed is:

1. A constant-current polarization voltage detecting method for use in a Karl-Fischer's moisture content analysis, comprising:
    (a) delivering a predetermined pulse current including at least one pulse to a detecting electrode;
    (b) detecting a first polarization voltage after a lapse of a predetermined time from the time of initiating the delivery of the at least one pulse of the pulse current;
    (c) detecting a second polarization voltage at a time subsequent to the detection of the first polarization voltage; and
    (d) obtaining a polarization voltage difference by subtracting the detected first polarization voltage from the detected second polarization voltage.

2. A constant-current polarization voltage detecting method according to claim 1, further comprising:
    integrating the polarization voltage difference during one cycle of current delivery and obtaining an integration value;
    ending measurement of the moisture content when said integration value of the polarization voltage difference reaches a predetermined value.

3. A Karl Fischer's moisture content measuring apparatus comprising:
    (a) means for delivering a constant current in a pulse form including at least one pulse to a detecting electrode immersed in a reaction liquid;
    (b) means for detecting a first polarization value after a lapse of a predetermined time from the time of initiating the delivery of the at least one pulse of the pulse current;
    (c) means for detecting a second polarization voltage at a time subsequent to the detection of the first polarization voltage;
    (d) means for calculating a polarization voltage difference value by subtracting the detected second polarization voltage from the detected first polarization voltage;
    (e) means for determining an end point of measurement of moisture content based on the calculated polarization voltage difference value; and
    (f) means for calculating a moisture content concentration from a result of the means for calculating.

4. A Karl-Fischer's moisture content measuring apparatus according to claim 3, wherein an end point of measurement of the moisture content is a time at which an integration of the polarization difference value in one cycle of current delivery, reaches a predetermined value.

5. A Karl Fischer's moisture content measuring apparatus according to claim 4, wherein said predetermined time is 0.1–200 ms.

6. A Karl Fischer's moisture content measuring apparatus according to claim 5, wherein the Karl Fischer's moisture content measuring apparatus is used in volumetric titration.

7. A Karl Fischer's moisture content measuring apparatus according to claim 5, wherein the Karl Fischer's moisture content measuring apparatus is used in coulometric titration.

8. A Karl Fischer's moisture content measuring apparatus according to claim 4, wherein the Karl Fischer's moisture content measuring apparatus is used in volumetric titration.

9. A Karl Fischer's moisture content measuring apparatus according to claim 4, wherein the Karl Fischer's moisture content measuring apparatus is used in coulometric titration.

10. A Karl Fischer's moisture content measuring apparatus according to claim 3, wherein said predetermined time is 0.1–200 ms.

11. A Karl Fischer's moisture content measuring apparatus according to claim 10, wherein the Karl Fischer's moisture content measuring apparatus is used in volumetric titration.

12. A Karl Fischer's moisture content measuring apparatus according to claim 10, wherein the Karl Fischer's moisture content measuring apparatus is used in coulometric titration.

13. A Karl Fischer's moisture content measuring apparatus according to claim 3, wherein the Karl Fischer's moisture content measuring apparatus is used in volumetric titration.

14. A Karl Fischer's moisture content measuring apparatus according to claim 3, wherein the Karl Fischer's moisture content measuring apparatus is used in coulometric titration.

* * * * *